(12) United States Patent
Vadis

(10) Patent No.: US 7,549,391 B2
(45) Date of Patent: Jun. 23, 2009

(54) INSECT HABITAT AND RETAIL RECEPTACLE

(75) Inventor: Gordon J. Vadis, Ham Lake, MN (US)

(73) Assignee: The Bug Company of Minnesota, Ham Lake, MN (US)

( * ) Notice: Subject to any disclaimer, the term of this patent is extended or adjusted under 35 U.S.C. 154(b) by 78 days.

(21) Appl. No.: 11/040,386

(22) Filed: Jan. 19, 2005

(65) Prior Publication Data
US 2005/0120963 A1 Jun. 9, 2005

Related U.S. Application Data

(63) Continuation-in-part of application No. 10/754,290, filed on Jan. 9, 2004, now abandoned.

(60) Provisional application No. 60/573,102, filed on May 20, 2004, provisional application No. 60/440,264, filed on Jan. 14, 2003.

(51) Int. Cl.
*A01K 29/00* (2006.01)
(52) U.S. Cl. ...................................................... 119/6.5
(58) Field of Classification Search ................. 119/6.5, 119/246, 248, 421, 452, 484; 206/521.1, 206/521.15, 521.4, 521.6; 229/162.1
See application file for complete search history.

(56) References Cited

U.S. PATENT DOCUMENTS

| | | | | |
|---|---|---|---|---|
| 903,161 A | * | 11/1908 | Barnes | 206/568 |
| 1,676,872 A | * | 7/1928 | Schurmann | 206/521.1 |
| 1,961,294 A | * | 6/1934 | Hassell | 206/521.6 |
| 1,990,145 A | * | 2/1935 | Swift, Jr. | 206/521.1 |
| D120,125 S | * | 4/1940 | Korda | D9/751 |
| 2,263,455 A | * | 11/1941 | Coyle | 229/120.15 |

(Continued)

FOREIGN PATENT DOCUMENTS

| GB | 2235434 A | * | 3/1991 |
| JP | 09002556 A | * | 1/1997 |

OTHER PUBLICATIONS

Goetz, Rudiger and Helfrich, Wolfgang; "The Egg Carton: Theory of a Periodic Superstructure of Some Lipid Membranes;" J. Phys. II France 6; Feb. 1996, pp. 215-223.

*Primary Examiner*—Yvonne R. Abbott
(74) *Attorney, Agent, or Firm*—James J. Paige; Nikolai & Mersereau, P.A.

(57) ABSTRACT

A live insect habitat that also serves as a retail receptacle for point of sale display of the insects. In particular, the invention comprises a cricket habitat and point of sale display receptacle for the sale of live crickets primarily for fishing bait and pet food purposes. The habitat/receptacle includes a housing having side walls with a sight window formed therein for purposes of permitting viewing of the inside of the housing and insect habitat from the outside. A habitat insert is located inside the housing and includes a multiple-sided member that partitions the interior space of the housing into discrete subspaces connected by passages giving the crickets ample room in which to crawl about. The housing and the habitat insert can be made of a moisture absorbent material in order to reduce the moisture content of the cricket environment. An item of cricket food is located in the housing whereby the retail habitat/receptacle has a prolonged shelf life while maintaining healthy live crickets.

26 Claims, 7 Drawing Sheets

U.S. PATENT DOCUMENTS

| | | | |
|---|---|---|---|
| 2,269,468 A * | 1/1942 | McKee | 206/521.6 |
| 2,458,737 A * | 1/1949 | Salkowitz | 229/90 |
| 2,548,001 A * | 4/1951 | Butterfill | 206/45.21 |
| 2,637,482 A * | 5/1953 | Broderick | 229/120 |
| 2,983,425 A * | 5/1961 | Rodriguez | 206/521.1 |
| 3,077,981 A * | 2/1963 | Gaspard | 206/223 |
| 3,202,337 A | 8/1965 | Cramer et al. | |
| 3,221,971 A * | 12/1965 | Reny | 206/521.8 |
| 3,260,236 A * | 7/1966 | Jones | 119/417 |
| 3,269,578 A * | 8/1966 | Lewis | 220/4.25 |
| 3,283,743 A * | 11/1966 | Dibelius | 119/6.5 |
| 3,292,513 A * | 12/1966 | Palmer | 493/354 |
| 3,311,284 A * | 3/1967 | Blais | 206/521.6 |
| 3,374,884 A * | 3/1968 | Chinkes | 206/459.5 |
| 3,392,902 A * | 7/1968 | Donovan | 206/521.1 |
| 3,406,816 A * | 10/1968 | Green et al. | 446/73 |
| 3,411,693 A * | 11/1968 | Macchi | 206/521.1 |
| 3,424,363 A * | 1/1969 | Donovan | 206/521.1 |
| 3,463,378 A * | 8/1969 | Van Daalen | 229/164.2 |
| 3,487,479 A * | 1/1970 | Grooms | 5/93.1 |
| 3,653,357 A * | 4/1972 | Sheidlower et al. | 119/6.5 |
| 3,747,831 A * | 7/1973 | Hanson | 206/277 |
| 3,760,939 A * | 9/1973 | Hawkyard | 206/577 |
| 3,845,898 A * | 11/1974 | Hackenberg | 229/120.13 |
| 3,870,221 A * | 3/1975 | Zeitter | 229/162.7 |
| 3,935,944 A * | 2/1976 | Wilson et al. | 206/569 |
| 3,942,710 A * | 3/1976 | Collie | 206/591 |
| 3,955,744 A * | 5/1976 | Casutt | 206/521.1 |
| D244,259 S * | 5/1977 | Bergstein | D9/418 |
| 4,046,309 A | 9/1977 | Poggiali | |
| 4,078,662 A * | 3/1978 | Volland | 206/564 |
| 4,081,122 A | 3/1978 | Hobson | |
| 4,109,786 A * | 8/1978 | Roccaforte et al. | 206/783 |
| 4,194,678 A * | 3/1980 | Jasper | 206/433 |
| 4,195,743 A * | 4/1980 | Emery | 217/26.5 |
| 4,377,252 A * | 3/1983 | Schillinger | 229/120.03 |
| 4,677,938 A * | 7/1987 | Tominaga | 119/421 |
| 4,699,311 A * | 10/1987 | Wallis | 206/521.2 |
| 4,981,109 A * | 1/1991 | Vaught | 119/61.5 |
| 5,000,118 A * | 3/1991 | Merritt et al. | 119/246 |
| 5,398,642 A * | 3/1995 | Harwich | 119/6.5 |
| 5,575,418 A * | 11/1996 | Wu et al. | 229/5.81 |
| 5,848,699 A * | 12/1998 | Pettersson | 206/521.1 |
| 5,855,187 A * | 1/1999 | Tominaga | 119/452 |
| 5,857,612 A * | 1/1999 | Smith et al. | 229/167 |
| 5,881,676 A * | 3/1999 | Brown et al. | 119/452 |
| D415,022 S * | 10/1999 | Gaudet et al. | D9/756 |
| 5,970,918 A * | 10/1999 | Bargy | 119/246 |
| 6,029,605 A * | 2/2000 | Licata | 119/246 |
| 6,105,535 A * | 8/2000 | Atamian et al. | 119/6.5 |
| 6,427,907 B1 * | 8/2002 | Espinoza et al. | 229/122 |
| 6,431,363 B1 * | 8/2002 | Hacker | 206/765 |
| D468,636 S * | 1/2003 | Weinstein et al. | D9/418 |
| 6,532,899 B1 * | 3/2003 | Hootman | 119/253 |
| D472,810 S * | 4/2003 | Gelardi et al. | D9/428 |
| 6,561,125 B1 * | 5/2003 | Lohsomboon | 119/6.5 |
| 6,622,867 B2 * | 9/2003 | Menceles | 206/771 |
| 6,625,922 B1 | 9/2003 | Ernsberger, IV | |
| D485,174 S * | 1/2004 | Amar et al. | D9/418 |
| 6,726,019 B2 * | 4/2004 | Leung | 206/769 |
| 6,814,279 B2 | 11/2004 | Jochens | |
| 6,926,152 B2 * | 8/2005 | Leung | 206/769 |
| 6,971,513 B2 * | 12/2005 | Weinstein et al. | 206/321 |
| D525,535 S * | 7/2006 | Rathbone | D9/757 |
| 2004/0112895 A1 | 6/2004 | Bartasevich et al. | |

* cited by examiner

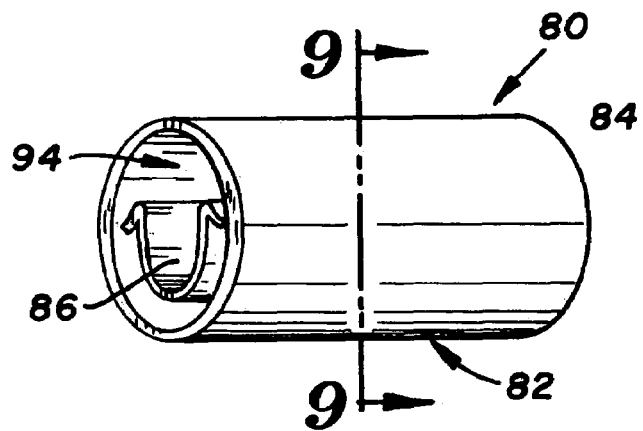
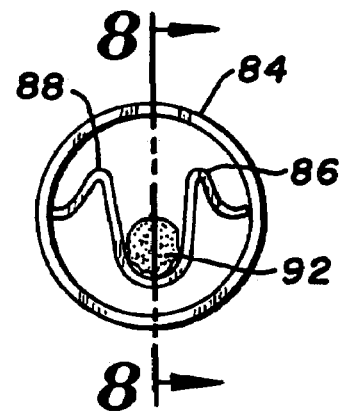
FIG.6  FIG.7
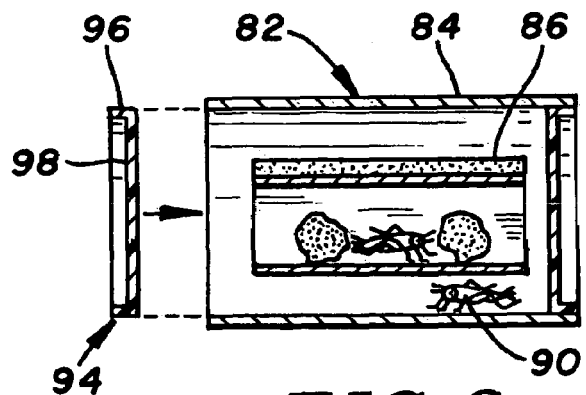
FIG.8
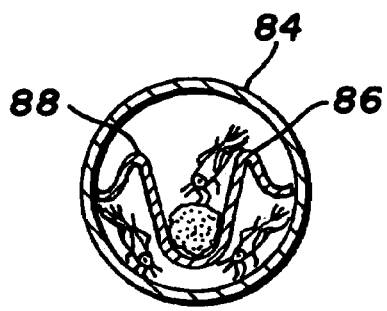
FIG.9

INSECT HABITAT AND RETAIL RECEPTACLE

CROSS REFERENCE TO RELATED APPLICATIONS

This application is a continuation-in-part of application Ser. No. 10/754,290 filed Jan. 9, 2004 which application claims the benefit of provisional application Ser. No. 60/440,264 filed Jan. 14, 2003. This application claims the benefit of provisional application Ser. No. 60/573,102 filed May 20, 2004.

BACKGROUND OF THE INVENTION

Live crickets are used as bait for fishing and for pet food. There is a substantial market for live crickets. Crickets are sold by mail order and shipped in crowded shipping boxes. At retail crickets are typically stored loose in a suitable bulk container such as an aquarium, wooden box, or plastic tub. Bulk inventories of crickets take up considerable amounts of floor space. Consequently there are typically more sizes of crickets available for a retailer to sell than can be offered. Quantities of loose crickets are scooped or otherwise derived from their bulk container such as an aquarium and given to the customer in a plastic bag or like receptacle. The crickets do not thrive well in the bulk container environment unless tended to with food and water on a periodic basis. Many do not survive. Those that do may not be particularly healthy if they have been neglected. The bulk container can create odor problems at the retail establishment. The display of loose crickets can be unappealing in bulk containers. Many crickets escape and run loose about the establishment or crawl into a neighboring establishment. Inventory control is a problem because it is difficult to accurately control numbers dispensed from bulk containers and because of cricket die-offs and escapes. Dispensing crickets from a bulk container is labor intensive for the retailer and inconvenient for both the employee and consumer.

SUMMARY OF THE INVENTION

The invention pertains to an insect habitat and retail receptacle for the purpose on the one hand of providing a healthy environment habitat for a number of live insects such as crickets and at the same time providing a retail point-of-sale or a mail order package for selling the crickets. The habitat/retail package includes a box or housing with a window or viewing opening covered by a suitable transparent material such as clear plastic or tightly woven screen. A habitat insert is located in the box. The insert is comprised of a multi-sided structure that partitions the inside of the housing into several discrete sub-spaces or compartments connected by passages. Structure of the insert can range from that of flat fiber board pieces to a convoluted structure having ridges or peaks and valleys that extend substantially from surface to surface of the box interior. The insert is constructed in such a way as to provide spaces for the crickets to crawl around from one surface of the habitat insert to another. The configuration of the insert permits insects to emerge into the light and outside view or to escape from the outside view and light from time to time as they seek out an area of comfort as their nature dictates. The insert can be of a moisture absorbent material. The insert can be a soft paper product material that is favored by crickets for chewing. The insert can be made of a nutritious material that can be consumed by the crickets. Nourishment in the form of a supply of food and water can be placed inside the box. A high moisture content food item such as a piece of carrot or commercially available cricket food can be placed inside of the box. The high moisture food item can be partially wrapped to retard moisture loss through evaporation.

The cricket habitat/package has an extended shelf life. The crickets are un-crowded and have continuous access to a food and water source that results in a generally healthier and "gut-loaded" cricket that is more nutritious to the animal being fed. The habitat/prepackage is a way to display and sell live crickets without the need to carry a bulk inventory of crickets. The habitat/package allows retailers to sell many cricket sizes where space considerations make similar bulk loose displays impractical. The prepackaged cricket habitats can be sold from a dispenser on a self-serve basis by which boxes are loaded into the dispenser from the top and dispensed from the bottom. This results in rotation of the stock. This also eliminates the need for an employee diversion to dispense crickets from a bulk container.

The housing can be made difficult to open so as to be tamper proof. The crickets, however, are clearly visible through the window of the housing. The housing can have a perforated punch-out opening pattern in a wall. The opening can be punched out when the box is placed in a pet environment where the crickets are intended as pet food. The crickets exit the box through the punched out opening over a period of time effectively managing the dispersion of pet food into the pet environment. When fed in this way, the pet environment is kept clean of the waste products like cricket feces, shed skins, food, and bedding that would normally be introduced when crickets are shaken from their container into an animal's living area.

The habitat insert in the box provides a climbing and nesting habitat for the crickets. It also provides areas and spaces for the more vulnerable crickets to hide from the others and from view through the window. The material of the insert and of the box absorbs and disperses condensation as may develop during shipping or as may be generated by live insects or the food and water supplement in the box. The window covering can be made of a micro-pore material that allows the escape of moisture. The window covering can be made of a tightly woven screen to do the same. The box and the insert provide dark areas for the crickets to escape from the light and from one another. Crickets generate organic debris in the form of shed skin and body waste as well as spent food and chewed bedding. The box can have collector panels or surfaces carrying a low tack adhesive that will collect and hold the debris so that it is not dispensed with the crickets. The adhesive is tacky enough to collect the debris but light enough so as not to inhibit cricket movement about the interior of the box.

The habitat insert creates additional surface area inside the box available for crickets to nest and climb upon. The insert helps the box to keep its shape and from being crushed, lending support from top-to-bottom, side-to-side and end to end.

According to another form of the invention a cricket habitat/retail package has a cylindrical housing. A convoluted habitat insert can be located in the housing. An adhesive tacky enough to collect the debris but light enough so as not to inhibit cricket movement about the interior of the box can be applied to the interior of the box. An end cover to the housing has a window for viewing the interior of the housing.

IN THE DRAWINGS

FIG. 6 is a side view in perspective of a cricket habitat/retail package according to a second form of the invention;

FIG. 7 is an end view of the cricket habitat/retail package of FIG. 6;

FIG. 8 is a sectional view of the cricket habitat/retail package of FIG. 7 taken along the line 8-8 thereof showing a cover removed;

FIG. 9 is a sectional view of the cricket habitat/retail package of FIG. 6 taken along the line 9-9 thereof;

Figure 1:
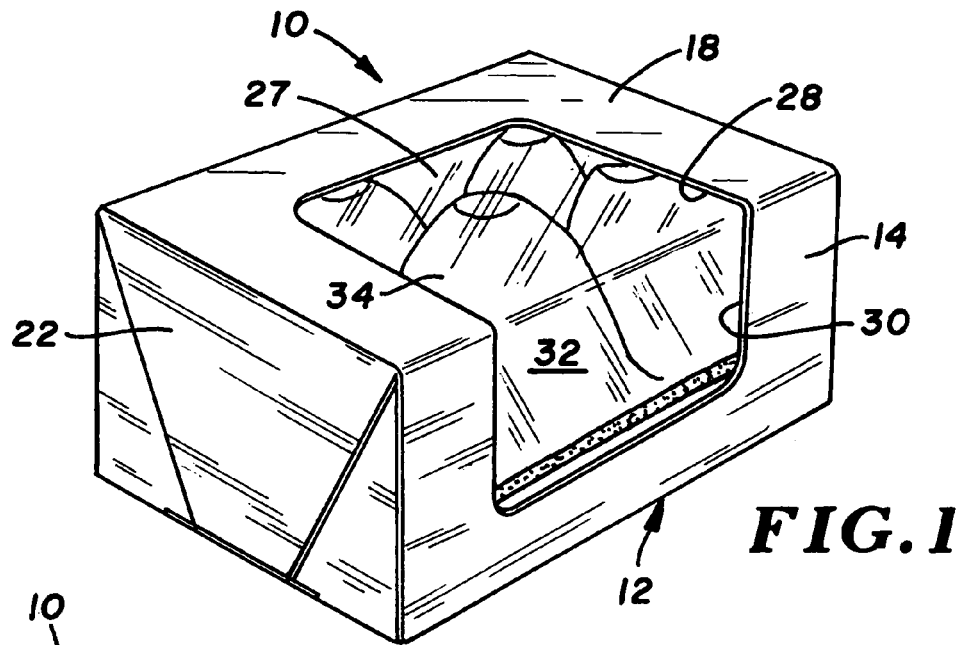
FIG. 1 is perspective view of a cricket habitat/retail package according to one form of the invention.

DESCRIPTION OF PREFERRED
EMBODIMENTS

Referring to FIGS. 1 through 4, there is shown an insect habitat and retail package indicated generally at 10. As described herein habitat 10 houses crickets although habitat 10 could house other species of insect as well. Habitat 10 includes a housing 12. Housing 12 can be formed of a moisture absorbent material such as a paperboard material. The term paperboard is used comprehensively to include, without limitation, cardboard, fiberboard, and similar products made from cellulose fiber and having a thickness greater than normal paper. Housing 12 can be fabricated of other material fabricated to permit the escape of moisture from the interior of the housing. This could include, for example, a perforated plastic. Housing 12 has an interior space or room for habitation by crickets. Housing 12 has a front wall 14, a back wall 16, a top wall 18 and a bottom wall 20 which define the interior habitat space for insects. The various walls are opaque. Housing 12 has end openings closed by end walls 22, 24 formed of end wall panels as will be more fully described. The end walls can be glued or constructed to fold together in such a way as to seal the package. The box can be of varying dimensions such as 1" to 3" high, 3" to 5" wide and 2" to 4" deep. By way of example, the box can typically be 3"×4"×2" and house 25 to 50 crickets.

Housing 12 has a sight window 27 for viewing crickets. Sight window 27 is a corner window. The sight window 27 is comprised of a first cutout opening 28 in the top wall 18 and an adjoining second cutout opening 30 in the front wall 14. A transparent material 32 covers the opening. The transparent material can be a continuous clear transparent paper or plastic material covering the cutout openings and traversing the corner formed at top wall 18 and front wall 14. Alternatively the covering material can be a tightly woven screen. The sight window 27 admits light and enables viewing of a portion of the interior of the housing 12 from the outside. The sight window can by way of example be 2" to 4" wide and have a dimension of 1" to 2" on the front wall of the housing, and 1½" to 2½" on the top wall.

In certain environments moisture accumulation in the air inside of housing 12 can be problematic. Crickets do not like moisture. The moisture can collect on an impermeable sight window covering material made of transparent plastic. Debris in the housing can adhere to this condensation. When the condensation dries, the debris is stuck to the window covering rendering it unsightly. One way to address this problem is through a window covering formed of a tightly woven mesh. Another way is through the use of a transparent covering material 32 formed of a plastic or plastic-like micro-pore material having micro-perforations of a size suitable to permit the escape of moisture from the interior of housing 12. Such a material can have micro-perforations in the order of magnitude of 70 micron to 300 micron. The micro-perforations serve to let moisture out of the housing 12. At the same time condensation of moisture on the inside of the window is avoided.

A cricket habitat environment is provided by a multisided habitat insert located inside the housing 12. The purpose of the habitat insert is to divide the space inside housing 12 into habitat spaces or compartments that are connected but separated from one another so as to provide multiple nesting areas for the crickets as well as areas of escape for the crickets from other crickets and from the light. The compartments are divided in such a manner that at least one compartment is shielded from direct light entering through the window 27 to provide at least one subdued lighting environment for the crickets.

Figure 2:
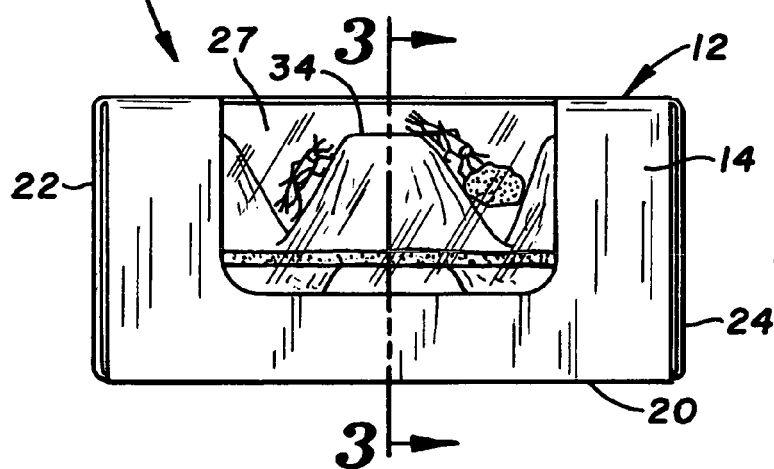
FIG. 2 is a front view of the cricket habitat/retail package of FIG. 1.
Figure 3:
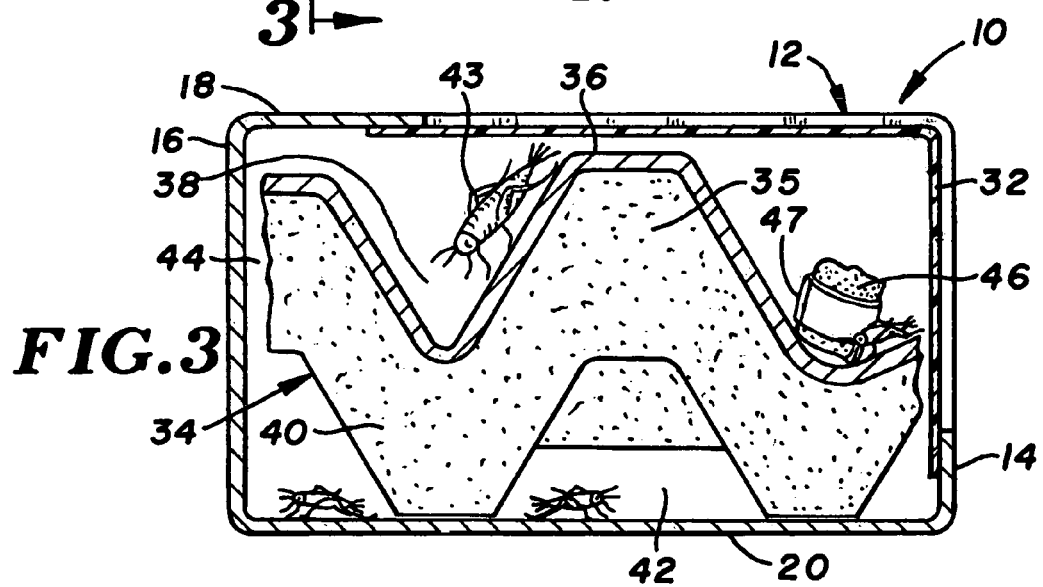
FIG. 3 is a sectional view of the cricket habitat/retail package of FIG. 2 taken along the line 3-3 thereof.

As shown in FIGS. 1 through 3, housing 12 has a habitat insert 34. Insert 34 substantially fills housing 12 from side-to-side, end-to-end and top-to-bottom. Insert 34 is a multi-sided partition of thin walls that can have flat, curved or convoluted surfaces or combinations thereof. Insert 34 can have a surface roughness 35. In the embodiment of FIGS. 1 through 3 insert 34 has a convoluted or egg carton shape structure. Habitat insert 34 formed this way has top and bottom surfaces characterized by peaks or ridges 36, 40 separated by valleys 38.

Housing 12 with insert 34 provides an ideal environment for crickets. The insert can be loosely disposed inside the housing 12 or can be constructed in such a way with formed holes or cutout openings as to provide access passages such as the passage 44 (FIG. 3) for crickets 43 to move from one surface area to another. The insert 34 offers a large surface area for the crickets 43 to crawl about. Crickets are known to be omnivorous whereby more dominant crickets will eat more vulnerable ones. The various surfaces of habitat insert 34 and the access passages 44 permit the more vulnerable crickets to escape to other areas. The insert partitions the interior of housing 12 into a multiple of subspaces or separate but connected compartments 42 for the crickets. Some compartments are more shielded than others from light entering the window opening. The various areas of insert 34 provide dark areas for live crickets 43 as well as areas of subdued light, both of which are preferred by crickets.

The material of the insert 34 can be moisture absorbent to absorb condensation that may develop in the package during shipping or otherwise. The insert 34 adds a measure of rigidity to the housing 12 by spanning the interior volume thereof. This is useful in terms of shipping the item and inventorying and dispensing the item in a store.

Insert 34 can be manufactured from a nutritious edible material such as a heavy gauge rice paper or wafer paper. As crickets are prone to chew the insert material, the provision of nutritious material is beneficial to the insects and consequently to animals they feed.

Food and water are provided in the housing 12. These can take the form of a high moisture food item such as a piece of carrot or such as the cricket food item indicated at 46 in FIG. 3. Crickets with such a food supply can survive for a period of at least seven days. The food supply can be periodically replenished. This prolongs the shelf-life of the product.

Food item 46 provides nourishment in the form of food and moisture. Water can evaporate from the exposed food item which can leave it dry and unappetizing to the cricket as well as depriving the cricket of needed water. As shown in FIG. 3 a wrap 47 can partially cover the food item 46 but leave portions exposed and accessible to the crickets. The wrap 47 can extend around the food item but leave the ends exposed. Wrap 47 can be formed of a suitable material such as a thin plastic sheet. Wrap 47 alternatively can be applied to the food and water supplement in the form of a suitable impermeable spray, or by dipping or by painted coating. Wrap 47 retards moisture loss from the food item through evaporation. This results in a longer lasting food item and extends the shelf life of the insect habitat/retail package.

It is desirable to eliminate pin-point light spots in housing 12 of the type that occurs at closure corners. Crickets are attracted to such light spots and tend to chew there and then escape through the chewed opening. The end walls of housing 12 and insert 34 contained in housing 12 address this problem.

Figure 4:
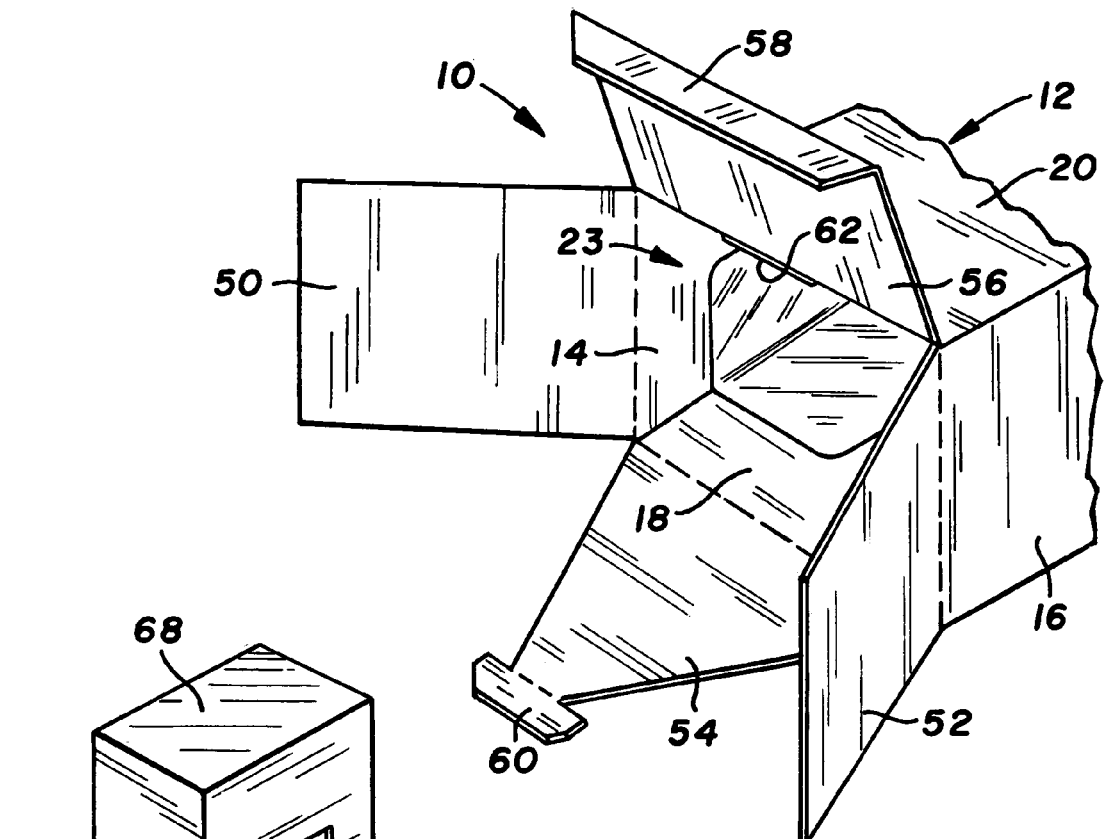
FIG. 4 is a view of the end of the box of the cricket habitat of FIG. 1 in an open configuration to show the closure system thereof.

As shown in FIG. 4, end wall 22 closes an end opening 23 to housing 12. End wall 22 includes opposing end panels 50, 52 that are pivotally attached to the edges of front and back walls 14, 16 adjacent end opening 23 and are positioned to fold over the end opening 23. Each of the end panels 50, 52 has a sufficient length and width to cover the end opening 23 when folded over it.

Top and bottom panels 54, 56 are connected to the edges of the top and bottom walls 18, 20 of housing 12 adjacent the end opening 23 and are foldable over the end panels. Bottom panel 56 has a length and width to substantially cover the end opening 23 when folded over the end panels 50, 52. Bottom panel 56 has an outer lip 58 that is inserted between the edges of the end panels in the closed position and the adjacent part of top wall 18.

Top panel 54 has tapered edges ending in a tongue 60 and is adapted to be folded over the end panels 50, 52 and bottom panel 56. A slot 62 is located at the intersection of the bottom panel 56 and the bottom wall 20. When the top panel 54 is folded over the end opening 23, the tongue 60 can be inserted into the slot 62 in order to secure closure 22 in the closed position. When closed light leakage is substantially eliminated.

Figure 5:
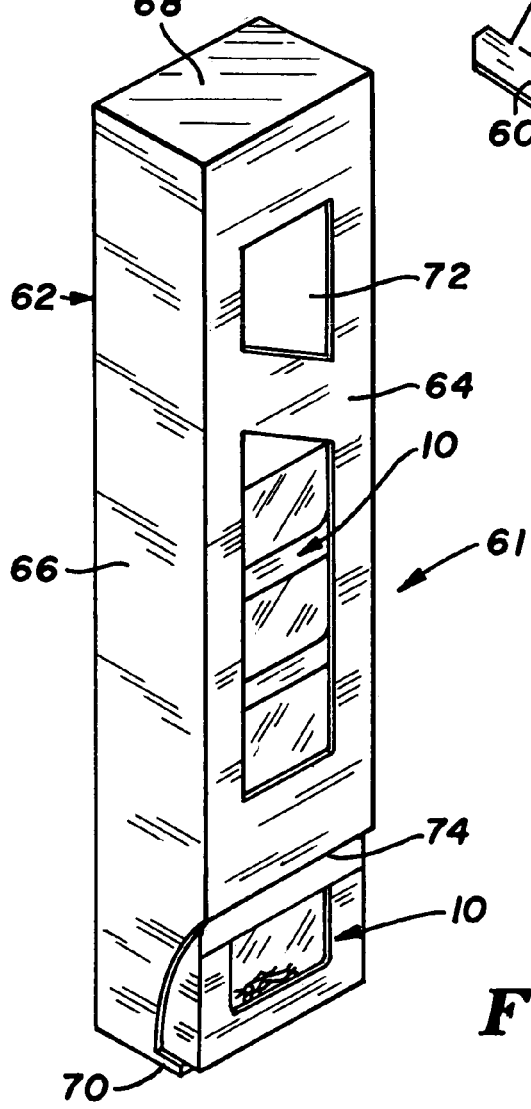
FIG. 5 is a front perspective view of a dispenser holding a number of cricket habitat/retail packages of FIG. 1 displayed for retail sale.

FIG. 5 shows a dispenser indicated generally at 61 for the cricket habitat/retail package of FIG. 1. The dispenser 61 includes a long, upright dispenser carton 62 having a rectangular cross-section with interior dimensions sufficient to accommodate the cricket habitat/retail packages 10. Dispenser carton 62 has a front wall 64, side walls 66 connected to a back wall (not shown). A hinged lid 68 closes the top opening formed at the top of the front, side and back walls. Opening the hinged lid 68 permits loading the dispenser carton 62 with packages 10 to be displayed for resale. A bottom wall 70 supports packages 10 held in the dispenser.

Front wall 64 has sight slots 72 for viewing packages 10 stored in the dispenser 61. Slots 72 also allow direct air exchange to vent air onto and moisture away from packages 10 stored in the dispenser. A dispensing opening 74 is located at the lower end of front wall 64. Dispensing opening 74 is large enough to permit packages 10 to be withdrawn or dispensed one at a time from the dispenser housing 62. As a package is removed from the dispensing opening 74 the next package drops down to the position of the previously withdrawn one. There is a continual rotation of stock. The carton 62 can be hung on a wall or placed in a stand and used as a self-service display. The carton covers the corners of the boxes that might otherwise permit light seepage. Darkened corners provide no incentive for crickets to chew isolated points. This reduces the likelihood of escape by way of chewing out of the box.

FIGS. 6 through 9 show a further embodiment of a cricket habitat/retail package according to the invention indicated generally at 80. Cricket habitat 80 includes a cylindrical box or housing 82 formed of fiber board or a material having properties similar to fiber board. Housing 82 is moisture absorbent and has opaque cylindrical sidewalls 84. A habitat insert 86 is located inside housing 82. Habitat insert 86 is a convoluted sheet material extending from side-to-side across the interior of housing 82 and is formed with openings or in such a way as to allow insects to crawl from one surface to another. Insert 86 has convolutions 88 providing a large surface area on which the live crickets 90 can crawl about. The ends of insert 86 are spaced from the ends of housing 80 permitting crickets 90 to crawl from one surface of the habitat insert 86 to the other. A food item 92 is lodged in the habitat insert 86. Sidewalls 84 and habitat insert 86 are a moisture absorbent material for purposes previously described.

Cricket habitat 80 includes a removable cover 94 secured in a first end of housing 82. Cover 94 is circular and frictionally fits in the open end of housing 82. Cover 94 includes a rim 96 that frictionally engages the interior walls of housing 82 at the end thereof. Rim 96 surrounds a cover base 98. Cover base 98 is a sight window formed of a transparent material such as a transparent plastic or tightly woven screen so as to permit viewing of crickets inside the housing 82 from the exterior thereof. Cover rim 96 and cover base 98 can be formed of a single piece of transparent material.

The second end of housing 82 is closed. It can be closed by a second friction-fit removable cover 102. Second cover 102 can be transparent or opaque. Alternatively the second end of housing 82 can be closed by a permanent closure means.

Figure 10:
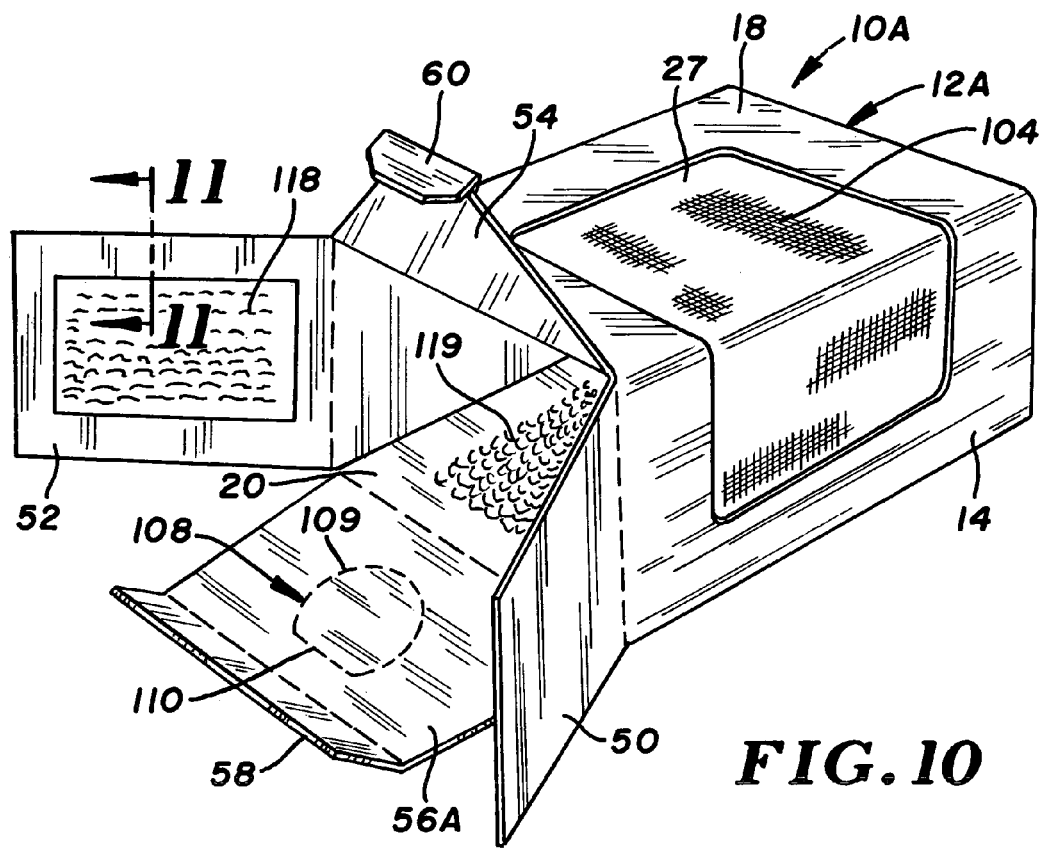
FIG. 10 is a perspective view of a modification of the cricket habitat/retail package of FIG. 1 with the habitat insert omitted for purposes of clarity.
Figure 12:
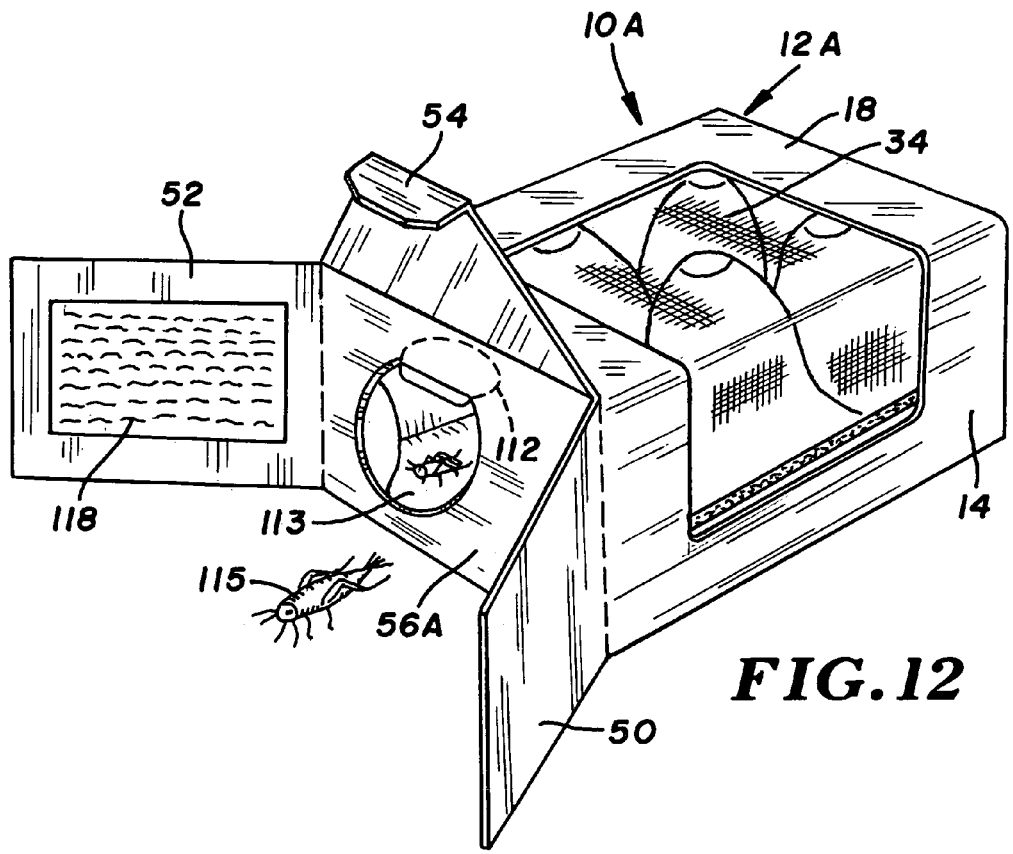
FIG. 12 is another view of the cricket habitat/retail package of FIG. 10 with an insert included showing an end panel closed and a punch-out opening created in a housing wall.

FIGS. 10 and 12 show a modification of the insect habitat and retail package of FIG. 1 indicated generally at 10A. In FIG. 10 the habitat insert is removed for purposes of clarity. The package 10A includes a housing 12A with an interior space for habitation by the insects. The housing 12A has a front wall 14, a top wall 18 and a sight window 27. An end of the housing or box 12A is closable by opposing end panels 50, 52 attached to the edges of the front and back walls of the housing 12A for folding between open and closed positions. Top and bottom panels 54, 56A are connected to the edges of the top and bottom walls 18, 20 of housing 12 and are foldable over the end panels as previously described.

A perforated pattern for a punch-out egress opening is formed in a wall of the housing 12A. The purpose of an egress opening is to allow the crickets to exit the housing 12A one at a time in a contained pet environment as opposed to simply broadcasting the crickets about the pet environment. Reptile pets such as lizards enjoy stalking food prey. An egress opening from the habitat housing will provide amusement to the reptile that will excitedly monitor the opening waiting for prey. Alternatively the egress opening permits a user to shake the housing 12A in salt-shaker like fashion to distribute crickets in a desired amount and location.

A punch-out egress opening pattern can be located on any convenient wall of housing 12A. As shown in FIG. 10, a punch-out egress opening pattern 108 is formed in the bottom panel 56A of one of the end closures of the housing 12A. The punch-out pattern includes a perforation line 109 that describes an intended opening, and a linear fold line 110. The ends of perforation line 109 connect to the ends of fold line 110. The perforation line 109 describes a closed pattern with the fold line 110 in the shape of the intended egress opening.

Until use the area described by the perforation line 109 is intact with the rest of the bottom panel 56A. At the time of use, pressure is applied to the area bordered by the perforation line 109. Referring to FIG. 12, under the influence of pressure applied, the perforation line gives way to form a door 112 which can be pivoted about the fold line 110 to create an egress opening 113. Alternatively the perforation line 109 could describe the entire intended egress opening whereby the door 112 would simply be completely punched out and removed.

As shown in FIG. 12, the bottom panel 56A is moved to covering relationship over the open end of housing 12A with the remaining end panels 50, 52, 54 out of the way. Crickets 115 can randomly exit the housing 12A by wandering through the egress opening 113. Crickets can also be distributed by shaking the housing 12A with the egress opening 113 facing down so that the crickets fall out.

Insects including crickets generate a considerable amount of debris in the form of shed skin and organic waste. In the confined space of housing 12A such debris can accumulate and become undesirable particularly upon dispensing the crickets from the box. The housing 12A includes one or more collector surfaces or panels to collect and accumulate the debris. As shown in FIG. 10, the housing 12A includes a first collector surface or panel 118 installed on the interior surface of an end panel 52 which will face the interior of housing 12A when closed. A second collector panel 119 is located on the bottom wall 20 of housing 12A and is exposed to the interior thereof. A collector panel can be located on any convenient exposed interior surface including exposed interior walls or the surfaces of the habitat insert.

Each collector panel includes a cold or light adhesive layer to attach and collect insect debris. The adhesive is a low tack adhesive that does not stick very strongly. The adhesive is tacky enough to adhere to and collect the insect debris, but not so adherent as to unduly impede the movement of the crickets in the housing.

Figure 11:
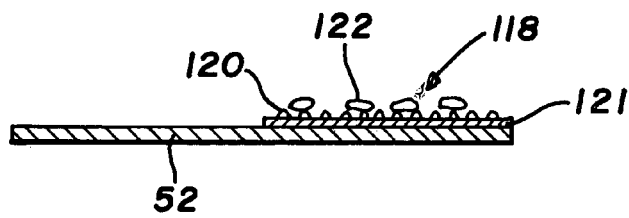
FIG. 11 is an enlarged sectional view of a portion of the cricket habitat/retail package of FIG. 10 taken along the line 11-11 thereof.

As shown in FIGS. 10 and 11, the collector panel 118 includes a substrate or carrier 121 fixed to the interior surface of the end panel 52. The carrier 121 carries an adhesive layer 120 of the type described above. The adhesive layer is effective to collect insect debris 122 so that it will not tumble about and out of the interior of housing 12A while not unduly inhibiting insect movement about the housing 12A. A low tack adhesive approximately as tacky as that used on Post-It Note® brand note pads has been found to be satisfactory.

Alternatively a collector panel can be comprised of an adhesive layer applied directly to a surface in lieu of being applied to a substrate fixed surface. The adhesive of collector panel 119 is applied directly to the surface of the housing wall 20 by suitable means such as brushing or spraying.

Figure 13:
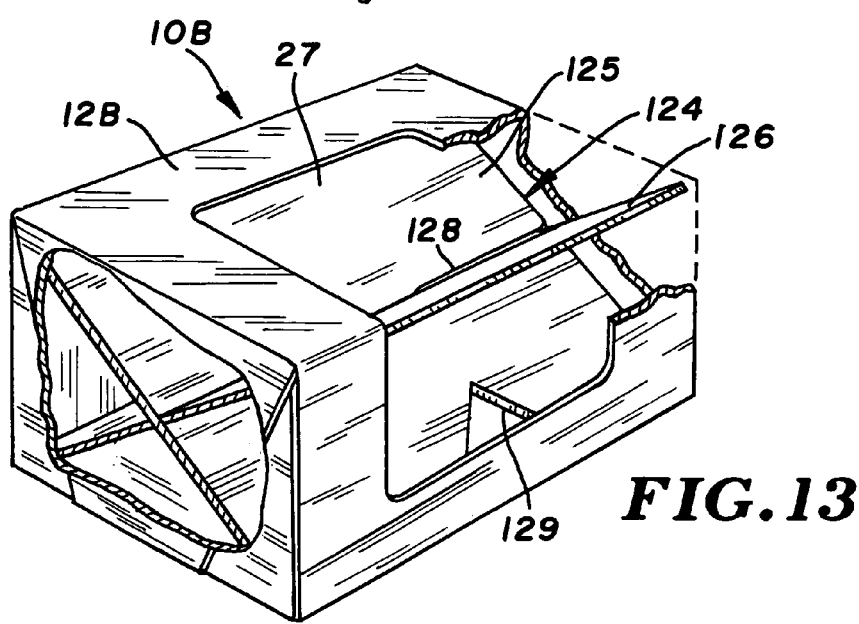
FIG. 13 is a view of a cricket habitat/retail package having a modification of a habitat insert and having a portion of the package housing removed for purposes of illustration.

FIG. 13 shows a further embodiment of a cricket habitat and retail receptacle indicated generally at 10B. Package 10B has a housing 12B that contains a habitat insert 124. Habitat insert 124 is comprised of insert panels 125, 126. A first panel 125 extends from an upper rear corner of the housing 12B to a lower forward corner. The second panel 126 extends from the upper forward corner of the housing 12B to the lower rear corner. The panels centrally intersect. The panels can intersect by engagement of centrally located mutually aligned slots 128. Together the panels 125, 126 substantially fill the interior of the housing 12B and partition it into separate habitat compartments, one or more being shielded from direct light entering the window 27. Openings 129 are formed at various locations in the panels 125, 126 in order to provide passages from one compartment to another. The habitat insert panels 125, 126 can be formed of a moisture absorbent paperboard product as previously described, or an edible material that is nutritious for the crickets. The partitions can have a thickness that is approximately equal to that of the thickness of the sidewalls of the housing 12B.

Figure 14:
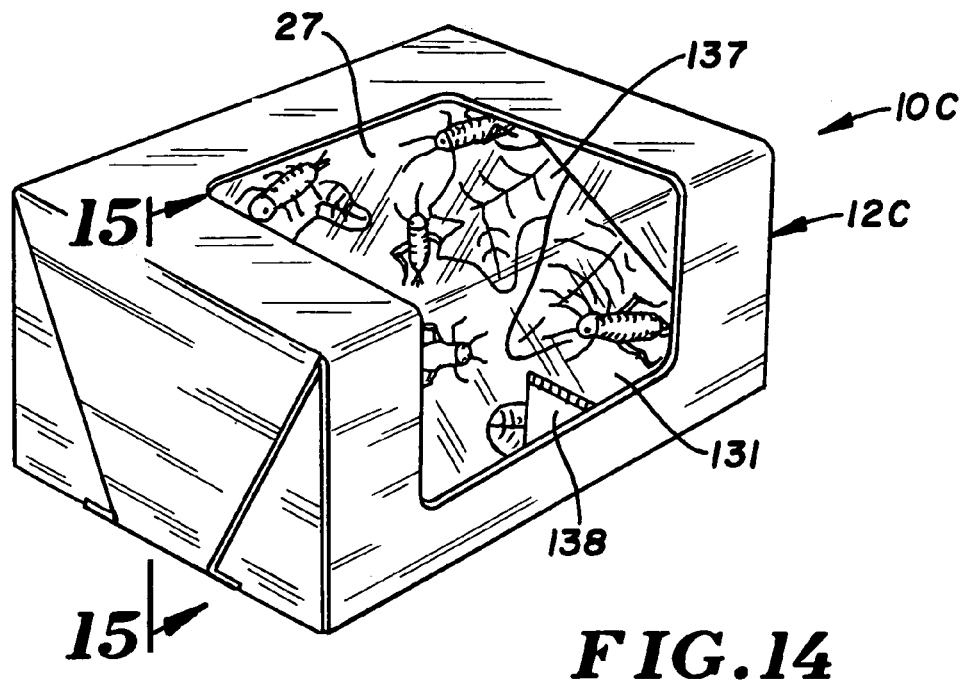
FIG. 14 is a view in perspective of a habitat/retail package having another modification of a habitat insert.
Figure 15:
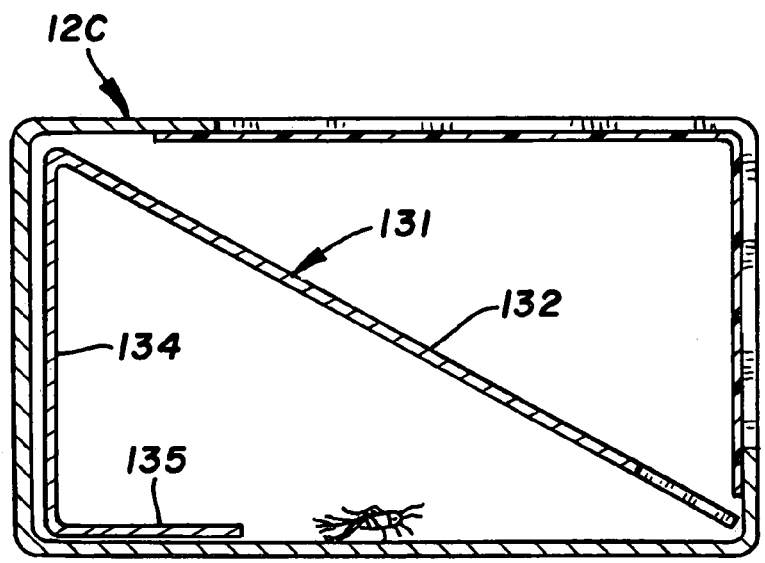
FIG. 15 is a sectional view of the habitat/retail package of FIG. 14 taken along the line 15-15 thereof.

FIGS. 14 and 15 show another embodiment of a cricket habitat and retail receptacle. Habitat 10C includes a box-like housing 12C with a sight window 27. A habitat insert 131 is located in the housing 12C. Habitat insert 131 includes a partition panel 132 that spans the width of housing 12C and extends from the upper rear corner to the lower forward corner. A rear leg 134 extends from the upper edge of the partition panel 132 horizontally to the lower rear corner of housing 12C. Foot 135 extends forward from the lower edge of the leg 134. The leg 134 and foot 135 serve to support partition panel 132 in place in the housing 12C. A passage opening 138 is provided to permit the cricket to travel from one partitioned area of housing 12C to another.

The front face of the partition panel 132 can carry a design such as the camouflage design shown in FIG. 14 for viewing through the window 27. The camouflage design can take the form of foliage such as leaves along with crickets crawling among the leaves. The camouflage design is aesthetically pleasing and conveys to the prospective customer the nature of the habitat/retail package 10C.

Figure 16:
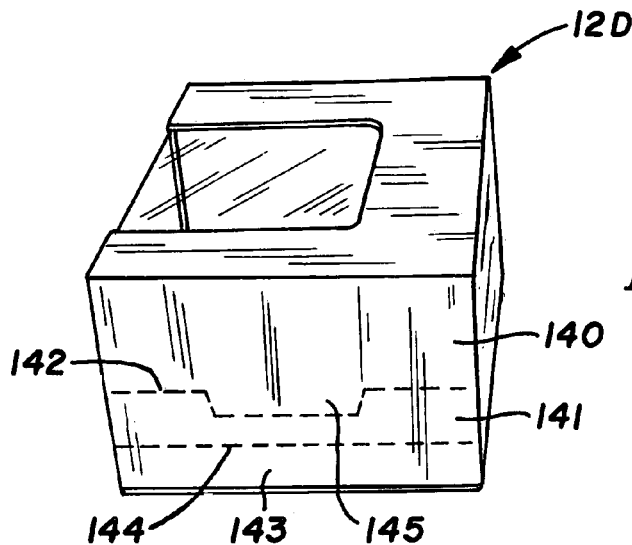
FIG. 16 is an end view of a habitat/retail package with a modified end closure having a tear-away strip.
Figure 17:
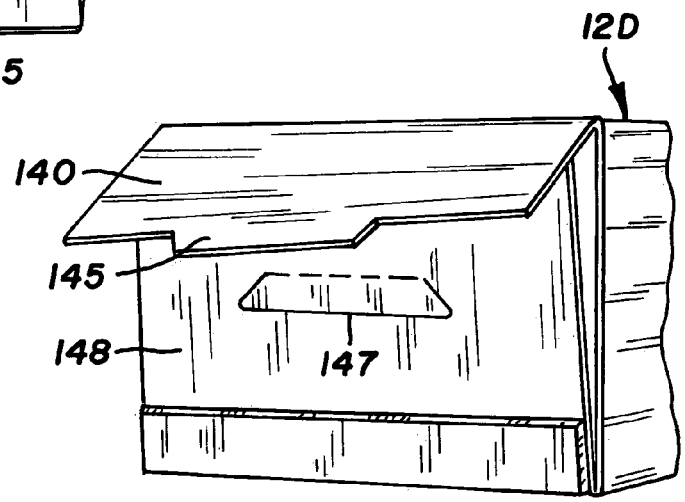
FIG. 17 is an end view of the habitat/retail package of FIG. 16 with the tear-away strip removed and preparatory to reclosing the box.
Figure 18:
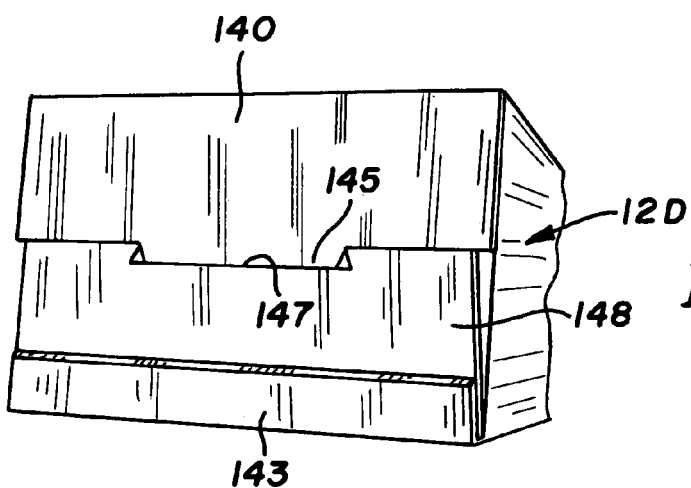
FIG. 18 is an end view of the habitat/retail package of FIG. 17 closed.

An alternative end closure for the cricket habitat/retail receptacle is shown in FIGS. 16-18. A housing 12D has an outer end panel 140. The lower edge 143 of panel 140 is glued to the next adjacent panel 148 to securely close the end of the box. Panel 140 includes a tear strip 141 that extends horizontally across the width of the end panel 140. An upper perforation line 142 and a lower perforation line 144 define tear strip 141. The upper perforation line 142 is indented to define a closure tab 145. The next adjacent panel 148 has a horizontal slot 147. The slot 147 is positioned to receive the closure tab 145.

In use, the retail receptacle package initially has the tear strip 141 intact on the outer panel 140. In lieu of having to rip the panels apart against the glue, the tear strip 141 is simply torn away from the outer panel 140. The upper portion of the panel 140 can be pivoted away from the box end. The remaining end panels can be folded open for access to the interior of the housing 12D.

The housing 12D is closed by folding the upper panel on 140 to a position where the closure tab 145 is poised over and inserted into the closure slot 147.

The embodiments of the invention in which an exclusive property or privilege is claimed are defined as follows:

1. An insect habitat and point of sale package comprising:
a rectangular housing made of paperboard material and having side walls that define an interior habitat space for insects;
a separate habitat insert disposed inside the habitat space of the housing; said insert comprised as a multisided structure formed in an egg carton shape having convoluted surfaces partitioning the habitat space into discrete subspaces to accommodate insects residing in the habitat space;
said housing including a top wall and a front wall adjacent the top wall;
a window in the housing, said window comprised of an opening cut out of the top wall and the front wall of the housing and a transparent material covering the opening; and
an item of insect food located in the habitat space.

2. The insect habitat of claim 1 wherein:
said habitat insert is formed of a moisture absorbent material.

3. The insect habitat of claim 1 wherein:
said box has a top wall, bottom wall, and front and back walls, and at least one closeable open end;
closure means for closing the open end of the box including opposable end flaps, each of a size to cover the end opening, and top and bottom flaps foldable over the end flaps in covering relationship to the end opening, and means to secure the top and bottom flaps in place folded over the end flap.

4. The insect habitat of claim 1 wherein:
said habitat insert fits loosely in the housing permitting insects to move from one surface to another.

5. An insect habitat and point of sale package comprising:
a rectangular box-like housing having connected top and bottom walls and front and back walls and end closures defining an interior space for a habitat space for live crickets;
a habitat insert located in the interior space of the housing and formed of a two sided sheet material having moisture absorbing characteristics;
said sheet material having a convoluted surface forming a plurality of peaks and valleys partitioning the habitat space into discrete subspaces accessible to crickets in the housing;
a sight opening in at least one wall of the housing;
a transparent material covering the sight opening so that crickets inside of the housing can be seen from outside of the housing;
a piece of insect food located inside the housing;
closure means for end openings comprised as end flaps foldable over the end openings, and top and bottom flaps foldable over the end flaps.

6. The insect habitat of claim 5 wherein:
said window in housing comprises a sight opening located in the top wall of the housing and a sight opening located in the front wall of the housing joining the sight opening in the top wall of the housing, and said transparent material covering the sight opening in the top wall of the housing and the sight opening in the front wall of the housing.

7. The insect habitat of claim 6 wherein:
said habitat insert formed of an egg carton type structure.

8. The insect habitat of claim 5 wherein:
said box is made of cardboard.

9. The insect habitat of claim 8 wherein the interior habitat space is configured to house a plurality of insects.

10. An insect habitat and point of sale package comprising:
a housing having opaque walls that define an interior habitat space for insects;
a window in a wall of the housing, said window comprised of an opening cut out of a wall of the housing and a transparent material covering the opening;
a habitat disposably inserted in the habitat space of the housing, said insert comprised as a multisided structure partitioning the habitat space into subspaces with passages between subspaces, with at least one subspace shielded from direct light from said window to allow insects to hide from other insects and from view through the window;
said habitat insert made of a moisture absorbent material; and
an item of food located in the habitat space.

11. The insect habitat of claim 10 wherein:
said housing is a rectangular box formed of a paperboard material including a top wall, a front wall and end walls, said window formed in the top wall and front wall.

12. The insect habitat of claim 10 wherein:
the habitat insert is made of a nutritious material edible by the insects.

13. The insect habitat of claim 10 wherein:
the habitat insert is made of a paperboard material.

14. The insect habitat of claim 10 wherein:
the food item is partially wrapped.

15. The insect habitat of claim 10 wherein:
said habitat insert is formed in an egg carton shape.

16. The insect habitat of claim 15 wherein:
the habitat insert is made of a nutritious material edible by the insects.

17. The insect habitat of claim 10 wherein:
said housing is a generally rectangular box formed of a paperboard material;
said box having a top wall, bottom wall, and front and back walls, and, at least one open end closed by an end wall that includes panels movable between open and closed positions;
said end wall including opposable end panels, each of a size to cover the end opening, and top and bottom panels foldable over the end panels in covering relationship to the end opening, and means to secure the top and bottom panels in place folded over the end panels.

18. The insect habitat of claim 10 wherein:
said transparent material covering the window opening is a clear plastic material.

19. The insect habitat of claim 10 wherein:
said habitat insert has a convoluted shape.

20. The insect habitat of claim 10 wherein:
said habitat insert has at least one flat partition panel.

21. The insect habitat of claim 10 wherein the interior habitat space is-configured to house a plurality of insects.

22. An insect habitat and point of sale package comprising:
a housing having walls and end openings closed by end walls that define an interior habitat space for insects and made of a material fabricated to permit the escape of moisture from the interior habitat space;
a separable habitat insert disposably located in the interior space and comprised as a multisided structure partitioning the interior habitat space into subspaces with passages between subspaces;

a piece of high moisture insect food located in the interior habitat space;

wherein the interior habitat space is configured to house a plurality of insects.

23. A habitat and point-of-sale package for confinement of a plurality of live insects, shipping the confined live insects to a point-of sale, displaying the live insects at the point-of-sale, nourishing the live insects during confinement, and releasing the live insects from confinement to allow them to be eaten by other animals, comprising:

(a) a rectangular housing made of two sided sheet material having a thickness greater than normal paper and fabricated to permit the escape of moisture from the interior space, the material selected from the group consisting of paperboard, cardboard, fiberboard, cellulose fiberboard, perforated plastic, and other materials fabricated to permit the escape of moisture;

(b) the housing defining an interior habitat space for live insects and having (i) opaque top, bottom, front, and back walls, (ii) two end walls, at least one of which has an open end, (iii) the open end having panels movable between open and closed positions comprising a first opposable end panel of a size to cover the open end and a second opposable end panel of a size to cover the open end, the first opposable end panel foldable over the open end and the second opposable end panel foldable over the first opposable end panel, a bottom panel foldable over the second opposable end panel, an outer lip on the bottom panel for insertion between a top wall and the top ends of the first and second opposable end panels, a slot in the bottom panel adjacent to the bottom wall, a top panel foldable over the bottom panel, and a tongue on the top panel for insertion into the slot to seal and thereby tamper proof the housing, (iv) a corner window in the housing, the corner window comprised of a first cutout opening in the top wall and an adjoining second cutout opening in the front wall, (v) a transparent material covering the opening, the transparent material selected from the group consisting of clear transparent paper, clear transparent plastic, plastic-like micro-pore material having micro-perforations, tightly woven screen mesh, and other material that allows the escape of condensation from the housing and prevents insects from leaving or entering the housing, and (vi) a perforated pattern in a wall of the habitat and point-of-sale package to punch-out for release of the confined living insects from the housing for consumption by another animal;

(c) a habitat insert configured to allow live insects to climb and have multiple nesting compartments, the habitat insert located and loosely fit in the habitat space of the housing, the habitat insert comprised of a structure (i) having multiple rough surfaced thin side walls that substantially extend to all interior surfaces of the housing, (ii) formed of a moisture absorbent, nutritious, edible material selected from the group consisting of heavy gauge rice paper, wafer paper, soft paper, or a combination thereof, (iii) having flat, curved, convoluted top and bottom surfaces or combinations thereof that form a plurality of ridges, peaks, and valleys which partition the habitat space into discrete compartment subspaces to accommodate insects residing in the habitat space and to provide rigidity to the housing, (iv) having passages between the discrete compartment subspaces that are formed between the habitat insert and the housing due to the loose fit of the habitat insert in the housing and/or by openings between the rough surfaced sides of the discrete compartment subspaces, thereby permitting live insects to move from one compartment subspace to another, and (v) having at least one compartment subspace shielded from direct light coming through the window in the housing so live insects may hide from other live insects and avoid being viewed through the window; and (d) sufficient high moisture live insect food located in the habitat space selected from the group consisting of (i) commercially available insect food, (ii) carrots, (iii) insect food partially wrapped with an impermeable membrane such as a thin plastic material, a spray coating, a dipped coating, or a painted coating, and (iv) the nutritious, edible habitat insert material, whereby live insects in the habitat and point-of-sale package have continuous access to the food and water during confinement.

24. An insect habitat and point of sale package comprising: (a) a rectangular housing made of paperboard material and having top and bottom walls, front and back walls, and side walls that define an interior habitat space for insects; (b) the housing having at least one closure means for closing an open end wall; (c) of the box including opposable end flaps, each of a size, to cover the end opening, and top and bottom flaps foldable over the end flaps in covering relationship to the end opening, and means to secure the top and bottom flaps in place folded over the end flap; (d) a habitat insert located in the habitat space of the housing; (e) the insert comprised as a multisided structure in an egg carton shape having convoluted surfaces partitioning the habitat space into discrete subspaces to accommodate insects residing in the habitat space; (f) the habitat insert configured to fit loosely in the housing permitting insects to move from one surface to another; (g) the habitat insert formed of a moisture absorbent material; (h) the top wall and the front wall of the housing adjacent to one another; (i) a window in the housing, the window comprised of an opening cut out of the top wall and the front wall of the housing; (j) a transparent material covering the window opening; and (k) an item of insect food located in the habitat space available to the insects during their confinement in the habitat and point of sale package.

25. An insect habitat and point of sale package comprising: (a) a rectangular cardboard box-like housing made of cardboard having connected top and bottom walls and front and back walls and end closures defining an interior space for a habitat space configured to house a plurality of live crickets; (b) a habitat insert located in the interior space of the housing and formed of a two sided sheet material having moisture absorbing characteristics; (c) the sheet material of the habitat insert comprised of a multisided structure of a plurality of peaks and valleys having convoluted surfaces partitioning the habitat space into discrete subspaces accessible to crickets in the habitat space; (d) a window in the housing comprising a sight opening in at least one wall of the housing; (v) a transparent material covering the sight opening so that crickets inside of the housing can be seen from outside of the housing; (vi) a piece of insect food located inside the housing; (vii) the habitat insert made of a nutritious material edible by insects; and (viii) closure means for end openings comprised as end flaps foldable over the end openings, and top and bottom flaps foldable over the end flaps, wherein the housing is configured to house a plurality of insects.

26. The insect habitat and point of sale package of claim 25, wherein the sight opening in the at least one wall of the housing comprises: (a) a sight opening located in the top wall of the housing and a sight opening located in the front wall of the housing joining the sight opening in the top wall of the housing and the transparent material covering the sight opening in the top wall of the housing and the sight opening in the front wall of the housing.

* * * * *